United States Patent
Morrison et al.

(10) Patent No.: US 6,300,104 B1
(45) Date of Patent: Oct. 9, 2001

(54) SECRETORY IMMUNOGLOBULIN PRODUCED BY SINGLE CELLS AND METHODS FOR MAKING AND USING SAME

(75) Inventors: Sherie L. Morrison; Kote R. Chintalacharuvu, both of Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/095,385

(22) Filed: Jun. 10, 1998

Related U.S. Application Data
(60) Provisional application No. 60/050,969, filed on Jun. 19, 1997.

(51) Int. Cl.$^7$ ................................................. A61K 39/29
(52) U.S. Cl. .................... 435/70.21; 435/70.1; 435/70.2; 435/320.1; 435/326; 435/328; 435/339; 424/141.1; 424/147.1; 424/133.1; 530/387.1; 530/808
(58) Field of Search ............................ 435/70.21, 320.1, 435/70.2, 70.1, 326, 328, 339; 424/147.1, 141.1, 133.1; 530/387.1, 808

(56) References Cited

U.S. PATENT DOCUMENTS
5,534,411 * 7/1996 Weltzin .
5,959,177 * 9/1999 Hein et al. ........................... 800/288

FOREIGN PATENT DOCUMENTS
WO 89/07142 8/1989 (WO) .
WO 97/42313 11/1997 (WO) .

OTHER PUBLICATIONS

Michetti, et al. (1991) Immunology of Milk an d the Neonate 310:183–185.
Kracji, et al. (1989) Biochemical and Biophysical Research Communications 158(3):783–789.
Mazanec, et al., (1987) J. Virol. 61:2624.
Mazanec, et al. (1989) J. Immunol. 142:4275.
Renegar, et al. (1991) J. Immunol. 146:1972.
Brown, et al. (1970) J. Clin. Invest. 49:1374.
Lindh, (1975) J. Immunol. 114:284.
Hirt, et al. (1993) Cell 74:245–255.
Lullau, et al. (1996) J. Biol. Chem. 271:16300.
Ma, et al. (1995) Science 268:716–719.
J.F. Piskurich, et al. (1995) J. Immunol. 154:1735–1747.
Ma, et al. (1998) Nature Med. 4(5):601–606.
Tamer, et al. (1993) Mol. Immunol. 30(4):413–421.
Chintalacharuvu, et al. (1996) J. Immunol. 157:3443.
Mostov, et al. (1993) Meth. Enzymol. 98:40.
Scheinderman, et al. (1989) Proc. Natl. Acad. Sci. USA 86:7561.
Knight, et al. (1975) J. Immunol. 115:595.
Weltzin, et al.(1989) J. Cell Biology 108:1673–1685.
Winner et al. (1991) Infect. Immun. 59:977.
Coloma et al. (1992) J. Immunol. Meth. 152:89.
Chintalacharuvu et al. (1991) J. Cell Physiol. 148:35.
Chintalacharuvu et al. (1993) Mol. Immunol. 30:19.
Oravax Report.
Chintalacharuvu and Morrison (1997) Proc. Natl. Acad. Sci. USA 94: 6364–6368.
Copy of International Search Report cited in Applicants' corresponding PCT Patent Application Serial No. PCT/US98/11975.

* cited by examiner

Primary Examiner—Marianne P. Allen
Assistant Examiner—Mary K. Zeman
(74) Attorney, Agent, or Firm—Gates & Cooper LLP

(57) ABSTRACT

Disclosed is a method of producing secretory Ig molecules. The method comprises transfecting a cell producing an Ig with a polynucleotide encoding an SC to fonn SC transfected Ig producing cells. Secretory Ig molecules, such as secretory IgA, can be used to treat or prevent infection.

19 Claims, 6 Drawing Sheets

SECRETORY IMMUNOGLOBULIN PRODUCED BY SINGLE CELLS AND METHODS FOR MAKING AND USING SAME

This application is based on U.S. provisional application serial No. 60/050,969, filed Jun. 19, 1997, the contents of which are incorporated herein by reference. Throughout this application various publications are referenced. The disclosures of these publications in their entireties are hereby incorporated by reference into this application in order to more fully describe the state of the art to which this invention pertains.

This invention was made with government support under grants CA16858, A129470 and A139187, awarded by the National Institutes of Health. The United States government has certain rights in this invention.

FIELD OF THE INVENTION

The present invention relates to secretory Ig molecules produced by a single cultured cell. The invention also relates to methods of producing and using the secretory Ig molecules.

BACKGROUND OF THE INVENTION

Secretory IgA (sIgA) is found in external secretions such as colostrum, respiratory and intestinal mucin, saliva, tears and genitourinary tract mucin and is often the first line of defense against infectious agents.

Monoclonal antibodies, specific for different diseases are available to combat infection. However, these monoclonal antibodies are predominantly of the IgG and IgM subclasses, which can be injected into a patient after an infection has been contracted. Monoclonal IgA would be a preferred agent and could be used for treatment and to prevent an infection before it enters the body of the host. Currently available monoclonal IgA is of limited therapeutic use since stable, secretory forms can only be produced in limited amounts and the non-secretory forms are unstable with relatively short half-lives in vivo.

IgA occurs in various polymeric forms including monomers ($H_2L_2$), dimers ($H_4L_4$) and even higher multimers ($H_{2n}L_{2n}$). In addition to heavy and light chains, the polymeric forms of IgA also usually contain J chains. The heavy, light and J chains are all produced by a lymphoid cell. Secretory IgA found at the mucosal surface also contains a secretory component (SC) which is attached during transport of the IgA across the epithelial lining of mucosal and exocrine glands into external secretions.

In vivo, sIgA is the product of two different cell types, the plasma cell and the epithelial cell. Plasma cells synthesize and assemble α H-chains and L chains with J chains into polymeric IgA. The polymeric IgA secreted by the plasma cell binds to a polymeric Ig receptor (pIgR) expressed on the basolateral surface of the mucosal epithelium. The IgA-pIgR complex is transcytosed to the apical surface. During transit, a disulfide bond is formed between the IgA and the pIgR. At the apical surface, the IgA molecule is released by proteolytic cleavage of the receptor. This cleavage results in a fragment, approximately 70,000 molecular weight, being retained on the IgA molecule. This fragment is the SC fragment, which is attached by disulfide bonds to the IgA molecule. The IgA-SC complex is thereby released into external secretions.

Passive administration of IgA could provide protection against a wide range of pathogens including bacteria and viruses such as HIV and respiratory syncytial virus. Hybridoma produced IgA antibodies applied directly to mucosal surfaces or transported into external secretions after injection into blood are protective, but have been found to be rapidly degraded (Mazanec et al., *J. Virol.* 61 2624, 1987; Mazanec et al., *J. Immunol.* 142 4275, 1989; Renegar et al., *J. Immunol.* 146 1972, 1991). In vitro, sIgA is more resistant to proteases than serum IgA (Brown et al., *J. Clin. Invest.* 49 1374, 1970; Lindh, *J. Immunol.* 114 284, 1975) suggesting that sIgA would be a more effective molecule for therapeutic use. However, co-culture systems containing hybridomas and polarized monolayers of epithelial cells (Hirt et al., *Cell* 74 245–255, 1993) and in vitro mixing of purified polymeric IgA (pIgA) and SC (Lullau et al., *J. Biol. Chem.* 271 16300,1996) have succeeded in producing only analytical quantities of sIgA.

Methods to purify large quantities of dimeric IgA (dIgA) and SC have been developed and noncovalent association of dIgA and SC has been shown by mixing dIgA and SC. However, the formation of disulfide bonds between dIgA and SC in vitro was inefficient. While the initial association between pIgA and SC is noncovalent, subsequent covalent association between IgA and SC requires cellular enzymes.

*Nicotiana tabacum* plants producing sIgA have been produced by successive sexual crossing of four transgenic *Nicotiana tabacum* plants producing: murine κ L chain; a hybrid Ig H chain containing an α chain with an additional IgG $CH_2$ domain; murine J chain; and rabbit SC. (Ma et al., *Science* 268 716–719, 1995). Though the assembly of sIgA in plants has been demonstrated, plant cells attach different sugar residues to proteins than do mammalian cells. This difference in glycosylation patterns may influence the biological properties of sIgA in vivo. In addition, the SC bound to IgA in the plant cells has been shown to be only 50 kDa, which is about 15–20 kDa lower than the expected molecular weight. These results suggest the SC fragment had undergone proteolytic degradation.

There is a need for a method of converting IgA produced in cell cultures, to sIgA which is more stable and more resistant to proteolytic attack. This sIgA should be able to be produced in amounts which make commercial production of the antibody for therapeutic use practical.

SUMMARY OF THE INVENTION

The invention provides a method for producing secretory Ig (sIg) molecules. The method permits the production of large quantities of sIg in a form which is stable and resistant to proteolysis. In addition, the method does not require the use of more than one cell type to produce the sIg. In one embodiment, the method comprises transfecting a cell producing an Ig with a polynucleotide encoding secretory component (SC) to form SC transfected Ig producing cells. The method can further comprise collecting, and optionally, purifying, a supernatant produced by the cell.

The secretory Ig and SC can be derived from the same species or from different species. In one embodiment, the cell endogenously produces Ig, while in an alternative embodiment, the cell is genetically modified to produce Ig. In one embodiment, the SC comprises the amino acid sequence shown in SEQ ID NO:4 or a congener thereof.

The cell can be a mammalian, avian, insect, bacterial or yeast cell. Examples of mammalian cells include, but are not limited to, human, rabbit, rodent (e.g., mouse, rat) and bovine cells. In preferred embodiments, the cell is a myeloma cell, chinese hamster ovary (CHO) cell, L cell, COS cell, fibroblast, MDCK cell, HT29 cell or a T84 cell.

The Ig molecule can be an IgA, IgM, IgG, IgD or IgE. Preferably, the Ig molecule is an IgA. The Ig molecule can be a domain-modified Ig molecule. Examples of domain-modified Ig molecules include, but are not limited to, an IgA molecule having the $C_H2$ domain of an IgG molecule, or an IgG molecule having the tailpiece of an IgM molecule. The Ig molecule can be modified by site-directed mutagenesis.

The invention provides a secretory Ig molecule produced by the method of the invention. In a preferred embodiment, the secretory Ig molecule is a secretory IgA.

The invention also provides a pharmaceutical composition comprising a secretory Ig molecule produced by the method of the invention and, optionally, a pharmaceutically acceptable carrier. In a preferred embodiment, the secretory Ig molecule is a secretory IgA.

The invention additionally provides a method of preventing infection in a subject comprising administering a secretory Ig molecule or composition of the invention to the subject. The subject can be a mammal, bird or fish. In one embodiment, the subject is a human. In one embodiment, the infection to be prevented is systemic or at a mucosal surface. The infection can be a bacterial, viral, mycoplasmal, mycobacterial, yeast or parasitic infection. Examples of viral infections include, but are not limited to, a human immunodeficiency virus (HIV), respiratory syncytial virus (RSV), herpes simplex virus (HSV), flu virus or cold virus infection.

Also provided is a method of treating an infection in a subject comprising administering a secretory Ig molecule or composition of the invention to the subject. The subject can be a mammal or bird. In one embodiment, the subject is a human. In one embodiment, the infection to be prevented is systemic or at a mucosal surface. The infection can be a bacterial, viral, mycoplasmal, mycobacterial, yeast or parasitic infection. Examples of viral infections include, but are not limited to, infection with a human immunodeficiency virus (HIV), respiratory syncytial virus (RSV), herpes simplex virus (HSV), flu virus or cold virus.

BRIEF DESCRIPTION OF THE DRAWINGS

FIG. 1 shows the assembly of chimeric sIgA in Sp2/O cells.

Lower panel shows a western blot analysis similar to that shown in the upper panel, except that blots were probed with rabbit anti-SC.

Figure 4A:
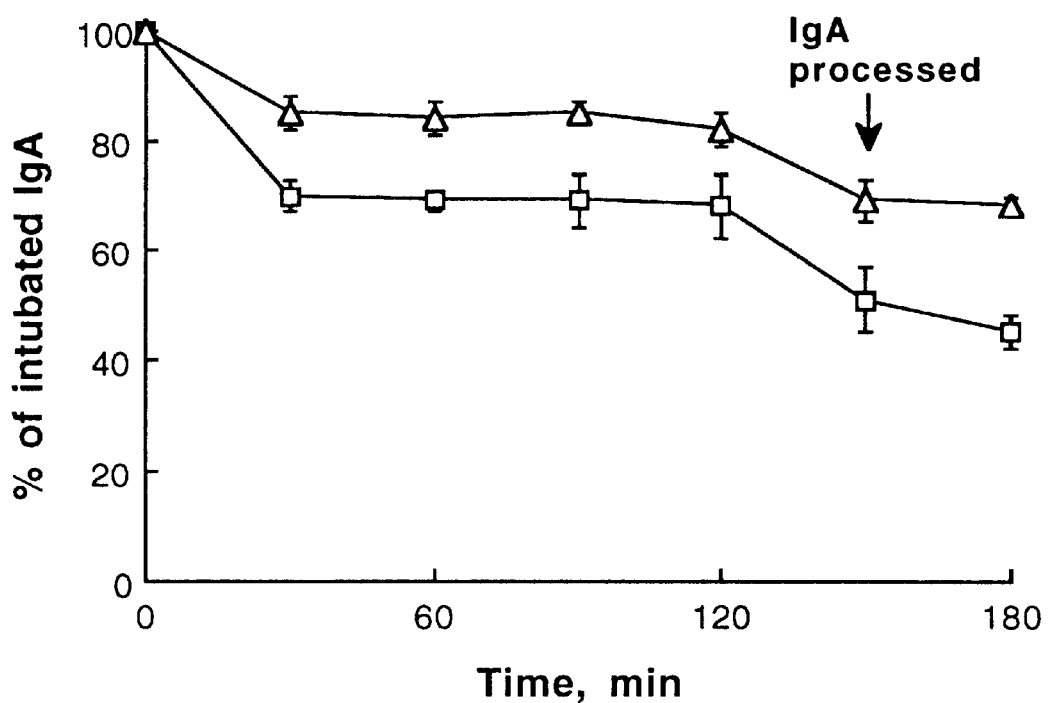

FIG. 4A shows in vivo stability of sIgA. $^{125}$I-labeled dIgA (□) and sIgA (Δ) were introduced directly into the stomach of BALB/c mice by intubation through polyethylene tubing attached to an 18-gauge needle on a hypodermic syringe. IgA remaining in the mice was determined by whole body counting.

Figure 4B:
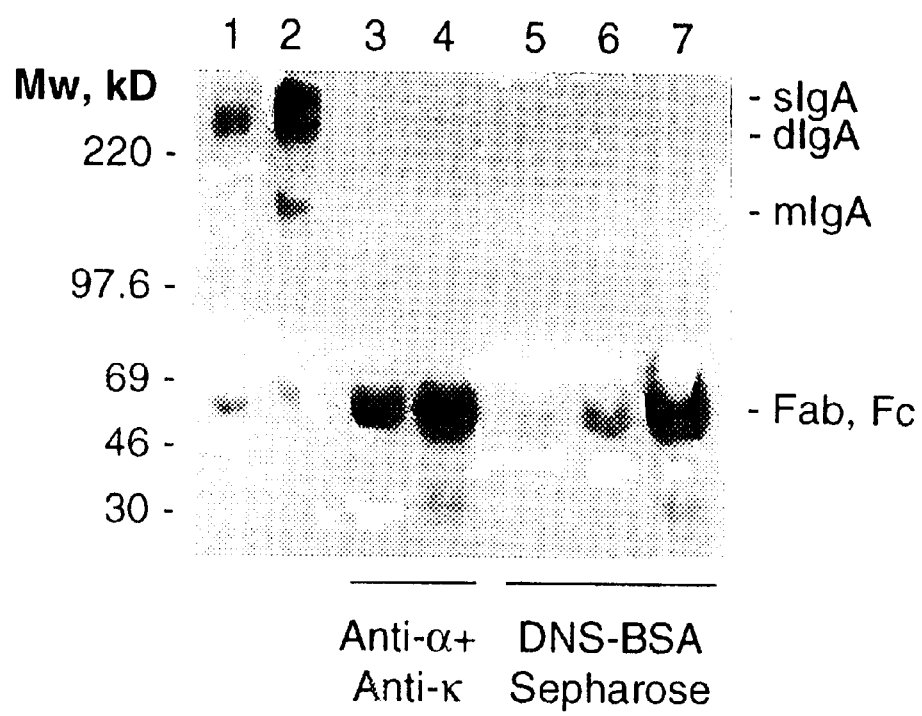

FIG. 4B shows in vivo stability of sIgA. After 150 min., a mouse intubated with dIgA (lanes 3 and 6) and a mouse intubated with sIgA (lanes 4 and 7) were sacrificed and the intestinal washings isolated and processed. IgA from the intestinal washes was immunoprecipitated with either anti-α and anti-κ antibodies (lanes 3 and 4) or with DNS-BSA-Sepharose (lanes 6 and 7). For comparison, mice injected intravenously with radiolabled dIgA were sacrificed after 3 hrs and the antigen specific IgA was precipitated from the intestinal washes as above (lane 5). Half of the precipitated proteins were analyzed by SDS-PAGE in phosphate gels. The gels were dried and exposed to Amersham Hyperfilm-MP for 48 hours. Also shown are the iodinated dIgA (lane 1) and sIgA (lane 2) used to intubate. The molecular mass protein standards are indicated on the left, the positions of sIgA, dIgA, mIgA and Fab and Fc are indicated at the right.

DETAILED DESCRIPTION

The invention provides a method for producing secretory Ig (sIg) molecules. The method permits the production of large quantities of sIg in a form which is stable and resistant to proteolysis. In addition, the method does not require the use of more than one cell type to produce the sIg. In one embodiment, the method comprises transfecting a cell producing an Ig with a polynucleotide encoding secretory component (SC) to form SC transfected Ig producing cells. The method can further comprise collecting, and optionally, purifying, a supernatant produced by the cell.

Definitions

All scientific and technical terms used in this application have meanings commonly used in the art unless otherwise specified. As used in this application, the following words or phrases have the meanings specified.

As used herein, "secretory Ig molecule" or "sIg" means an immunoglobulin molecule to which secretory component (SC) or a congener thereof is bound. The Ig molecule can be an IgA, IgM, IgG, IgD or IgE. IgA includes IgA1 and IgA2.

As used herein, "domain-modified Ig" means an immunoglobulin molecule having a substitution, deletion, duplication or rearrangement of substantially all of the amino acids of at least one of the domains of a constant region, including modification by site-directed mutagenesis. Examples of domain-modified Ig molecules include, but are not limited to, an IgA molecule having the $C_H2$ domain of an IgG molecule, or an IgG molecule having the tailpiece of an IgM or IgA molecule. Methods of preparing domain-modified Ig molecules are described in WO 89/07142.

As used herein, "secretory component" or "SC" means a protein fragment corresponding to the ectoplasmic domain of an IgA receptor. (The domains of SC are described in J. F. Piskurich et al., 1995, J. Immunol. 154:1735–1747.) In preferred embodiments, the SC is derived from a human or other mammal. In one embodiment, the SC has the amino acid sequence shown in SEQ ID NO:4.

As used herein, "congener" of SC means an SC molecule having one or more amino acid substitutions or deletions in the amino acid sequence shown in SEQ ID NO:4, yet retaining the ability to associate with an Ig molecule. The association can be a covalent bond or a non-covalent interaction. For example, one skilled in the art will appreciate that a deletion of all or a portion of one of the 5 domains of the amino acid sequence shown in SEQ ID NO:4 would not interfere with SC association with an Ig molecule. The domains of SC are described in J. F. Piskurich et al., 1995, J. Immunol. 154:1735–1747. Other variations of SC are possible.

As used herein, "vector" means a construct which is capable of delivering, and preferably expressing, one or more gene(s) or sequence(s) of interest in a host cell. Examples of vectors include, but are not limited to, viral vectors, naked DNA or RNA expression vectors, DNA or RNA expression vectors associated with cationic condensing agents, DNA or RNA expression vectors encapsulated in liposomes, and certain eukaryotic cells, such as producer cells.

As used herein, "expression control sequence" means a nucleic acid sequence which directs transcription of a nucleic acid. An expression control sequence can be a promoter, such as a constitutive or an inducible promoter, or an enhancer. The expression control sequence is operably linked to the nucleic acid sequence to be transcribed.

The term "nucleic acid" or "polynucleotide" refers to a deoxyribonucleotide or ribonucleotide polymer in either single- or double-stranded form, and unless otherwise limited, encompasses known analogs of natural nucleotides that hybridize to nucleic acids in a manner similar to naturally-occurring nucleotides. Unless otherwise indicated, a particular nucleic acid sequence optionally includes the complementary sequence.

As used herein, "pharmaceutically acceptable carrier" includes any material which, when combined with an Ig, allows the Ig to retain biological activity and is non-reactive with the subject's immune system. Examples include, but are not limited to, any of the standard pharmaceutical carriers such as a phosphate buffered saline solution, water, emulsions such as oil/water emulsion, and various types of wetting agents. Preferred diluents for aerosol or parenteral administration are phosphate buffered saline or normal (0.9%) saline.

Methods of Producing sIg

To produce SC in cells producing Ig, a polynucleotide which encodes the ectoplasmic domain (SC) of an IgA receptor is used. The polynucleotide preferably lacks the region encoding the transmembrane and the cytoplasmic domains of the IgA receptor. The polynucleotide can be modified and still encode SC or a congener thereof. In one embodiment, the polynucleotide encodes an SC having the amino acid sequence shown in SEQ ID NO:4. In one embodiment, the polynucleotide has the sequence shown in SEQ ID NO:3. In one embodiment, the coding sequence of the fragment has a silent mutation upstream of Glu589 (equivalent to Glu607 of SEQ ID NO:4) to delete a BamHi site in the SC coding region. A stop codon can be included downstream of Glu589, at amino acid 590, the position of normal SC processing. Those skilled in the art can identify and construct polynucleotides which encode congeners of the SC molecule that retain desired features of the parent molecule, e.g., ability to bind Ig molecules.

For example, it is a well-established principle of protein chemistry that certain amino acid substitutions, referred to as conservative amino acid substitutions, can frequently be made in a protein without altering either the conformation or the function of the protein. Such changes include substituting any of isoleucine (I), valine (V), and leucine (L) for any other of these hydrophobic amino acids; aspartic acid (D) for glutamic acid (E) and vice versa; glutamine (Q) for asparagine (N) and vice versa; and serine (S) for threonine (T) and vice versa. Other substitutions can also be considered conservative, depending on the environment of the particular amino acid and its role in the three-dimensional structure of the protein. For example, glycine (G) and alanine (A) can frequently be interchangeable, as can alanine and valine (V).

Methionine (M), which is relatively hydrophobic, can frequently be interchanged with leucine and isoleucine, and sometimes with valine. Lysine (K) and arginine (R) are frequently interchangeable in locations in which the significant feature of the amino acid residue is its charge and the differing pK's of these two amino acid residues are not significant. Still other changes can be considered conservative in particular environments.

For expression, the polynucleotide is cloned into an expression vector. Such vectors are well known to those skilled in the art. An expression control sequence, such as an Ig or viral promoter, is introduced upstream of the polynucleotide, and a polyA$^+$ signal is introduced downstream of the polynucleotide. Selection markers such as the his gene, or other suitable selectable marker well known to those skilled in the art, are included in the vector to allow selection of cells which are expressing the genes included on the vector after transfection of the vector into cells.

In use, the expression vector including the SC is transfected into cells expressing Ig, that may be expressed from endogenous genes. Alternatively, the genes necessary for expression of Ig may be introduced by gene transfection either before or after transfection with an SC vector. Transfection methods are well known in the art and such methods are suitable for use in the present invention. The cells expressing the expression vector are selected using the selectable marker incorporated into the expression vector or a vector used for co-transfection. Cells expressing the SC and the SC covalently bound to the Ig can be screened by ELISA assays or other suitable methods well known to those skilled in the art.

Secretory Ig, such as sIgA, is secreted into the media of the cell cultures which have been transfected with the expression vector. The media are collected and the sIg is purified from the media by methods well known to those skilled in the art.

The secretory Ig and SC can be derived from the same species or from different species. In one embodiment, the cell endogenously produces Ig, while in an alternative embodiment, the cell is genetically modified to produce Ig. Examples of cells that endogenously produce Ig include, but are not limited to, hybridomas, lymphomas, plasmocytomas and EBV transformed cells. A cell can be genetically modified to produce Ig by conventional methods, such as by transfection with a vector encoding an Ig molecule, either before or after transfection with an SC vector.

The cell can be a mammalian, avian, insect, bacterial or yeast cell. Examples of mammalian cells include, but are not limited to, human, rabbit, rodent (e.g., mouse, rat) and bovine cells. In preferred embodiments, the cell is a myeloma cell, a chinese hamster ovary (CHO) cell, L cell, COS cell, fibroblast, MDCK cell, HT29 cell or a T84 cell.

The Ig molecule can be an IgA, IgM, IgG, IgD or IgE. Preferably, the Ig molecule is an IgA. The Ig molecule can be a domain-modified Ig molecule. Examples of domain-modified Ig molecules include, but are not limited to, an IgA molecule having the $C_H2$ domain of an IgG molecule, or an IgG molecule having the tailpiece of an IgM or IgA molecule, including modification by site-directed mutagenesis.

The invention provides a secretory Ig molecule produced by the method of the invention. In a preferred embodiment, the secretory Ig molecule is a secretory IgA.

Compositions

The invention also provides a composition comprising a secretory Ig molecule produced by a method of the invention. In one embodiment, the composition is a pharmaceutical composition. In a preferred embodiment, the secretory Ig molecule is a secretory IgA.

The composition can comprise a therapeutically or prophylactically effective amount of an Ig molecule of the invention. The composition can optionally include a carrier, such as a pharmaceutically acceptable carrier. Pharmaceutically acceptable carriers are determined in part by the particular composition being administered, as well as by the particular method used to administer the composition. Accordingly, there is a wide variety of suitable formulations of pharmaceutical compositions of the invention. Compositions comprising such carriers are formulated by well known conventional methods (see, for example, Remington's Pharmaceutical Sciences, Chapter 43, 14th Ed., Mack Publishing Col, Easton, Pa. 18042, USA).

In one embodiment, the composition is administered topically. Examples of sites for topical administration include, but are not limited to, the oral cavity and eye, upper and lower respiratory tract, gastrointestinal tract, skin and urogenital regions. Topical administration of Ig molecules to the oral cavity is described in Ma et al., 1998, Nature Med. 4(5):601–606. In another embodiment, the composition is administered intranasally, for example, in the form of drops or spray. Intranasal or intravenous administration is a preferred method of administration.

Formulations suitable for parenteral administration, such as, for example, by intraarticular (in the joints), intravenous, intramuscular, intradermal, intraperitoneal, and subcutaneous routes, and carriers include aqueous isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

Methods of Using Secretory Ig

The invention additionally provides a method of preventing infection in a subject comprising administering a secretory Ig molecule or composition of the invention to the subject. The subject can be a mammal, fish or bird. In one embodiment, the subject is a human. In one embodiment, the infection to be prevented is systemic or at a mucosal surface. The infection can be a bacterial, viral, mycoplasmal, mycobacterial, yeast or parasitic infection. Examples of viral infections include, but are not limited to, HIV, RSV, HSV, flu virus and cold virus infection.

Also provided is a method of treating an infection in a subject comprising administering a secretory Ig molecule or composition of the invention to the subject. The subject can be a mammal, fish or bird. In one embodiment, the subject is a human. In one embodiment, the infection to be prevented is systemic or at a mucosal surface. The infection can be a bacterial, viral, mycoplasmal, mycobacterial, yeast or parasitic infection.

Viral infections that can be treated include, but are not limited to, those caused by hepatitis A, hepatitis B, hepatitis C, non-A, non-B hepatitis, hepatitis delta agent, CMV, Epstein-Barr virus (EBV), HTLV 1, HTLV II, FeLV, FIV, HIV I, RSV, HSV, flu virus and cold virus. Bacterial infections that may be treated include, but are not limited to, pneumonia, sepsis, tuberculosis, and Staphyloccoccus infections, among others. Parasitic infections that can be treated include, but are not limited to, malaria (caused by protozoa of the genus Plasmodium, and include *P. falciparum, P. malariae, P. ovale*, and *P. vivax*), sleeping (caused by trypanosomes), and river blindness.

The dose of sIg administrated to a subject, in the context of the present invention should be sufficient to effect a beneficial therapeutic response in the subject over time, or to inhibit infection. Thus, sIg is administered to a subject in an amount sufficient to alleviate, reduce, cure or at least partially arrest symptoms and/or complications from the disease or infection. An amount adequate to accomplish this is defined as a "therapeutically effective dose."

The dose will be determined by the activity of the sIg produced and the condition of the subject, as well as the body weight or surface areas of the subject to be treated. The size of the dose also will be determined by the existence, nature, and extent of any adverse side effects that accompany the administration of a particular sIg in a particular subject. In determining the effective amount of the sIg to be administered, the physician needs to evaluate circulating plasma levels, CTL toxicity, and progression of the disease.

Advantages of the Invention

The administration of sIg, such as sIgA, offers a method for immunotherapeutic prevention and treatment of infections. Treatment of humans with a sIgA produced in plant cells has been shown to protect against oral streptococcal colonization for at least four months (Ma et al., 1998, Nature Med. 4(5):601–606). Production of sIg using non-plant cells as provided by the methods of the invention is considerably more efficient than the multi-step process of fusing recombinant plant cells, and avoids alterations of the sIg produced by plant cells. IgA in secretory form is more effective than non-secretory IgA, such as the non-secretory IgA which failed to produce a statistically significant reduction in hospitilization for lower respiratory tract infection in Phase III trials conducted by OraVax, Inc. (Mar. 3, 1997 press release, available at http://www.oravax.com). The production of sIg using a single cell type allows for more efficient production on a commercially useful scale than is possible with the co-culture systems used by others.

EXAMPLES

The following examples are presented to illustrate the present invention and to assist one of ordinary skill in making and using the same. The examples are not intended in any way to otherwise limit the scope of the invention.

Example 1
Cloning Human Ectoplasmic Domain

To produce sIgA a gene coding for human pIgR was obtained from Dr. Charlotte S. Kaetzel (University of Kentucky, Lexington, Ky.). A fragment from pIgR containing only the ectoplasmic domain (SC) and lacking the transmembrane and the cytoplasmic domains was generated. A 1402 bp PCR fragment was generated using the complete human pIgR cDNA in pBluescript (Tamer et al., *Mol. Immunol.* 30 413–421, 1993, this article and all other articles cited herein are incorporated herein by reference) as template and the primers:

1. 5'-GGGCAGAACGGTGACCATCAACTGCCCTTT-3' (SEQ ID NO:1) and
2. 5'-AAGGAATTC CTACTCTGCAAAAAGCCTGGGGTCCTGAATGGC-3' (SEQ ID NO:2)

The second primer included a silent base change upstream of Glu589 to delete a BamHI site in the SC coding region to facilitate cloning. A stop codon, shown by underlining, followed by an EcoRI site downstream of Glu589 were also included. A stop codon was introduced at amino acid 590, the position of normal SC processing. The fragment was fused to a 1.42 kb Ig 3'-region with a polyA addition site. The PCR product was cloned into TA vector (Invitrogen) and the sequence was confirmed by sequencing. The complete human SC gene was generated by a three way ligation of the EcoRI-KpNI fragment including the Kozak sequence, the leader sequence and the 5'-SC sequence and KpNI-EcoRI PCR fragment into an EcoRI site of pBluescript II KS+containing Ig-polyA$^+$ signal. A 3.28 kb EcoRV-BamHI fragment containing the complete SC gene was ligated downstream of an Ig promoter in a pSV2 expression vector containing the his gene as a selection marker.

Example 2
Expression of Cloned Human Ectoplasmic Domain in Cells Secreting Mouse-Human Chimeric IgA1

Sp2/0 transfectants secreting monomeric and dimeric forms of mouse-human chimeric IgA1 have been previously reported (Chintalacharuvu et al., *J. Immunol.* 157 3443, 1996). Cells secreting mouse-human chimeric IgA1 were transfected with the SC expression vector by electroporation. Sp2/0 cells were plated in 96-well tissue culture plates in presence of Histidinol. The surviving colonies were screened for SC secretion by ELISA using goat anti-κ as the trapping antibodies and rabbit anti-human SC as the detecting antibody. The clone producing the highest quantity of sIgA was expanded and adapted to growth in serum free medium.

Figure 1A:
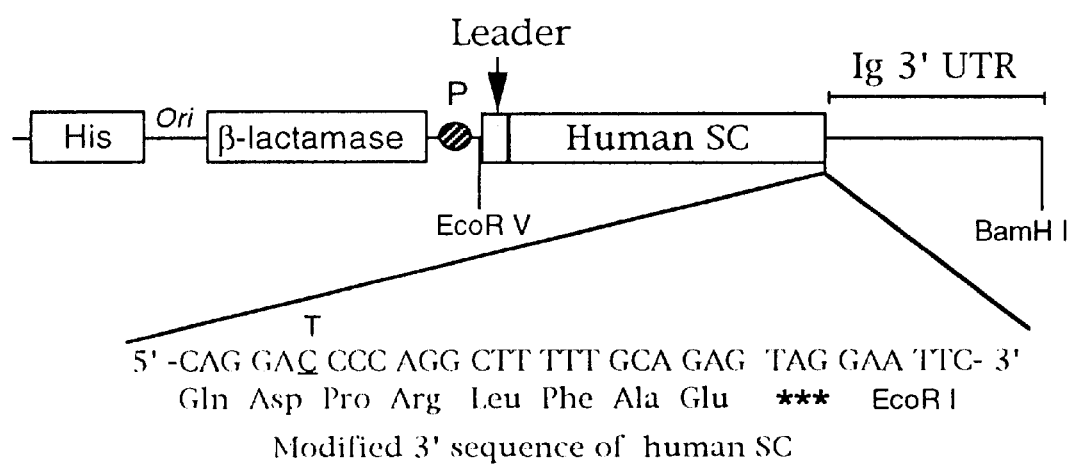
FIG. 1A is a schematic representation of a human SC'expression vector containing genes for histidinol and ampicillin resistance as well as a 1.82 kb human SC coding sequence.

Since SC is a cleavage product of the pIgR a stop codon was introduced at the site of cleavage (FIG. 1A). Murine transfectomas secreting mouse-human chimeric IgA1 specific for the hapten dansyl (Chintalacharuvu et al., *J. Immunol* 157 3443, 1996) were transfected with the SC expression vector by electroporation (Coloma et al., *J. Immunol. Meth.* 152 89, 1992). Transfectants synthesizing and secreting sIgA were identified by ELISA.

Example 3
Analysis of Culture Supernatants

The levels of sIgA in culture supernatants were determined by ELISA as described previously (Chintalacharuvu et al., *J. Immunol* 157 3443, 1996). Microtiter plates coated with dansylated BSA was used to capture sIgA. Bound sIgA was detected by incubation with rabbit antiserum to human SC (Chintalacharuvu et al., *J. Cell. Physiol.* 148 35, 1991) diluted 1:2000 in phosphate buffered saline (PBS) containing 1% (w/v) BSA (PBS-1% BSA). Bound rabbit antibody was detected using an alkaline phosphatase conjugated goat anti-rabbit IgG (Sigma Imm. Chem.) diluted 1:10,000 in PBS-1% BSA. Color was developed by adding 5 mg/ml of disodium p-nitrophenyl phosphate (Sigma Imm. Chem.).

Example 4
Pulse-Chase Experiments In Vitro

Pulse-chase experiments were used to analyze the assembly of the SC and IgA. About $6 \times 10^6$ cells secreting sIgA were pulsed with 75 $\mu$Ci of $^{35}$[S]cysteine for 20 min. followed by chase with 100 fold unlabeled cysteine. At the specified times, cells were cooled to 0° C. and pelleted by centrifugation. Cell lysates and supernatants were prepared as described by Mostov et al. (*Meth. Enzymol.* 98 40, 1983). SC and molecules covalently associated with SC were precipitated from cell lysates and supernatants with anti-SC followed by IgGSorb (Mostov et al., *Meth. Enzymol.* 98 40, 1983). The immunoprecipitates were analyzed by SDS-PAGE in 6% (w/v acrylamide) Tris-Glycine gels under nonreducing conditions. Immunoprecipitations with rabbit anti-human SC were performed under conditions such that only IgA covalently associated with SC was precipitated (Mostov et al., *Meth. Enzymol.* 98 40, 1983). The immunoprecipitates were analyzed by SDS-polyacrylamide gel electrophoresis (SDS-PAGE) in the absence (FIG. 1B) or the presence (FIG. 1C) of a reducing agent.

Figure 1B:
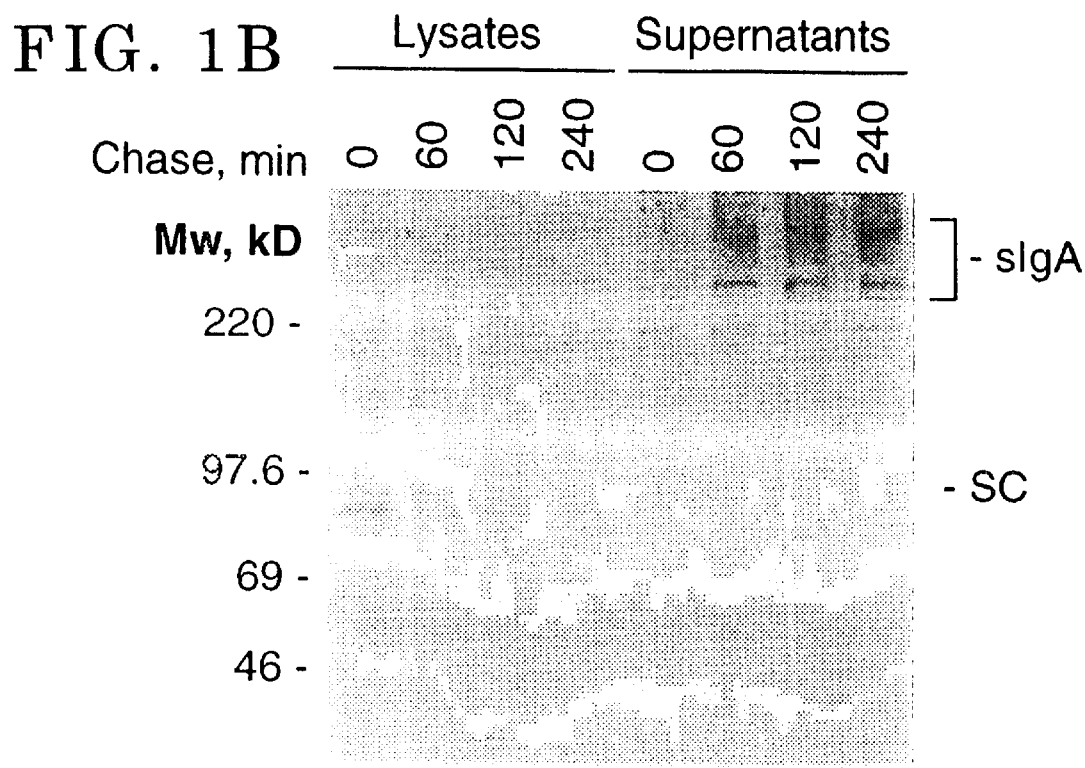
FIG. 1B shows the results of pulse-chase experiments used to analyze the assembly and secretion of SC. The molecular mass protein standards are indicated on the left, the positions of sIgA, SC, α, κ and J chain are indicated at the right.
Figure 1C:
FIG. 1C shows an analysis of immunoprecipitates in 12.5% (w/v acrylamide) Tris-Glycine gels under reducing conditions. The molecular mass protein standards are indicated on the left, the positions of sIgA, SC, α, κ and J chain are indicated at the right.

Immediately after the pulse a sharp band of SC with a Mr 77 kDa was precipitated from the cellular lysate; with time this band became diffuse indicating glycosylation of SC as it moved along the secretory pathway (FIG. 1B). Little covalently associated sIgA was observed within the cell although a small amount of H and L chains was observed following reduction of the immunoprecipitates (FIG. 1C). SC was efficiently secreted with 45% of the total SC being secreted into and found in the supernatant by 60 min. and 75% being secreted into and found in the supernatant by 4 hrs. Notably, virtually all of the SC was secreted covalently associated with sIgA. Only a minor band of free SC, with a Mr of 80 kDa, was observed in the supernatant. Densitometric analysis of the secreted proteins showed approximately four α chains were present per each molecule of SC and J chain suggesting that one molecule of J chain and SC were present per dIgA (data not shown).

Figure 2A:
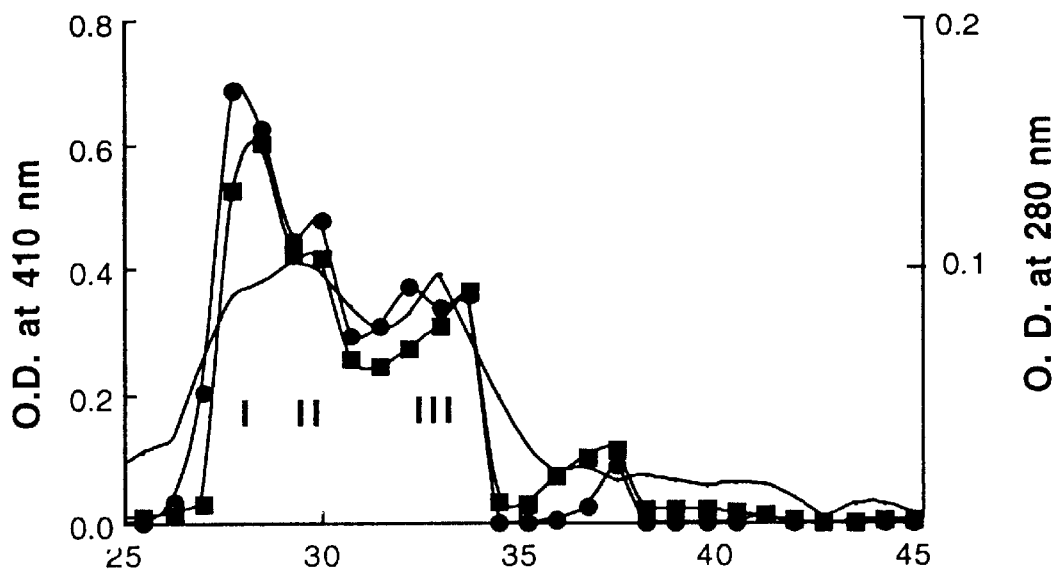
FIG. 2A shows an analysis of the composition of proteins secreted by transfectants synthesizing chimeric sIgA1. Three hundred microliters of 100-fold concentrated serum free medium was separated on two Pharmacia Superose 6 columns in series. The solid line indicates the protein profile at 280 nm. The fractions were analyzed by ELISA with IgA captured on dansylated-bovine serum albumin (DNS-BSA) coated microtiter plates and detected with rabbit anti-κ (□,■) or anti-SC (○,●) followed by goat anti-rabbit antibody conjugated to alkaline-phosphatase and substrate. The closed symbols (●,■) indicate the sIgA fractions and the open symbols (○,□) indicate the IgA1 fractions. The presence of dIgA and mIgA was confirmed by analysis of the fractions by SDS-PAGE.
Figure 2B:
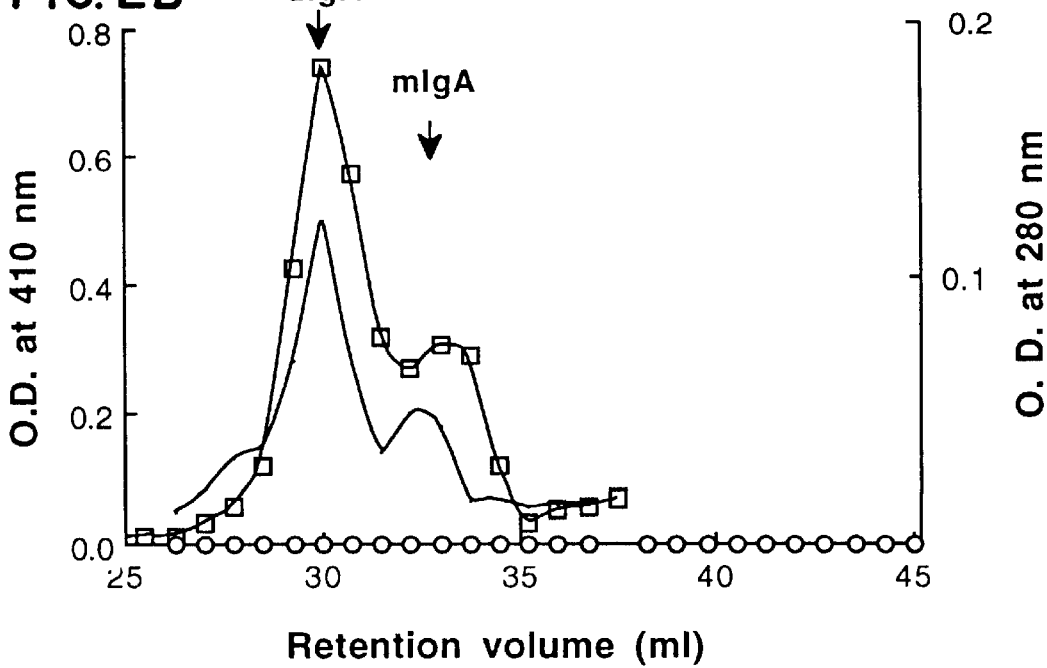
FIG. 2B shows an analysis similar to that shown in FIG. 2A, but of the composition of proteins secreted by transfectants synthesizing IgA1.

These results show that SC was covalently linked to IgA intracellularly just prior to the time of secretion. In the parental cell line, chimeric IgA1 dimerizes late in the secretory pathway (Chintalacharuvu et al., *J. Immunol* 157 3443, 1996), presumably when J chain was incorporated into the molecule (Koshland, *Ann. Rev. Immunol.* 3 425, 1985). In vivo, sIgA is assembled in the transcytotic pathway of epithelial cells (Brandtzaeg, *Scan. J. Immunol* 8 39, 1978; Brandtzaeg et al., *Nature* (London) 311 71, 1984). The assembly of sIgA in the transfected myeloma cells appears to take place in the Golgi apparatus when dIgA and SC are present together. Analysis of concentrated culture supernatant from a transfectant by gel filtration (Chintalacharuvu et al., *Mol. Immunol.* 30 19, 1993) yielded three overlapping peaks with retention volumes of 27.5, 29.5 and 33 ml FIGS. 2A–2B. When the fractions were analyzed by ELISA all three peaks were found to contain antibody and SC indicating association of SC with IgA. Supernatants from cells producing only IgA1 yielded two peaks corresponding to dIgA and monomeric IgA (mIgA). No reactivity was seen with anti-SC.

Figure 3:
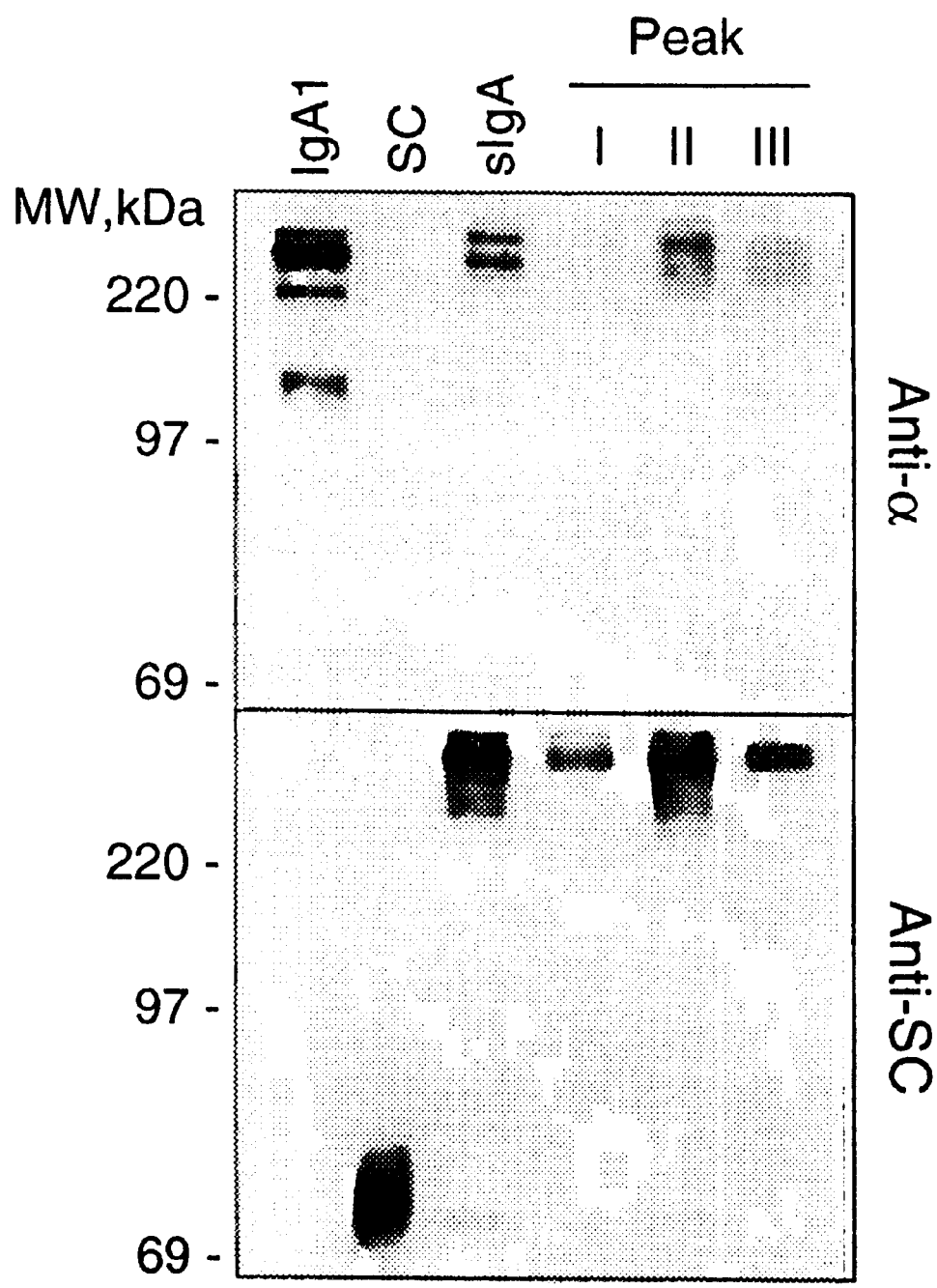
FIG. 3 upper panel, shows a western blot analysis of FPLC fractions. Fractions I, II, and III from the FPLC analysis shown in FIGS. 2A–2B were separated by SDS-PAGE in 6% (w/v acrylamide) Tris-Glycine gels and analyzed by Western blotting (Chintalacharuvu et al., *J. Immunol* 157 3443, 1996). Blots were probed with rabbit anti-α chain (Sigma Imm. Co.). Included for comparison are supernatants from transfectants synthesizing only IgA1, transfectants synthesizing only human SC and unfractionated culture supernatant from the cell line synthesizing sIgA.

To further characterize the peaks and to determine if covalent bonds were formed between dIgA and SC in sIgA, the fractions from each of the peaks were concentrated and analyzed by SDS-PAGE and Western blotting (FIG. 3). Anti-α detected a band with apparent Mr of 400 kDa in peak I and two bands of apparent Mr of 400 kDa and 320 kDa in peaks II and III and in the starting material. The 320 kDa band was also observed in supernatants derived from cultures of cells synthesizing only IgA1. Anti-SC detected the 400 kDa in all three peaks indicating that it corresponds to covalently associated sIgA with the 320 kDa band representing dIgA without attached SC. Free SC was observed in the supernatants of cell lines producing only SC. It is noteworthy that only a small amount of a 80 kDa protein corresponding to free SC was detected in both the unfractionated sIgA and in peak II indicating that the majority of SC synthesized by the transfectant was covalently associated with IgA. In vivo, IgA can be found with both covalently and noncovalently attached SC (Schneiderman et al., *Proc. Natl. Acad. Sci. USA* 86 7561, 1989; Knight et al., *J. Immunol* 115 595, 1975).

Example 5
In Vivo Stability of sIgA

To determine the in vivo stability of dIgA and sIgA, dIgA and sIgA proteins purified from culture supernatants by dansyl-Sepharose affinity chromatography were radiolabeled with $^{125}$I and introduced into the stomach of BALB/c mice by intubation. The elimination of IgA from the mice was followed by whole body counting (Zuckier et al., *Cancer* 73 794, 1994). dIgA was more rapidly eliminated than sIgA (FIG. 4A). At 150 min. post-intubation, mice were sacrificed and the intestinal contents isolated and processed.

The intestinal contents were isolated and processed by a modified method of Elson et al. (*J. Immunol. Meth.* 67 101, 1984). Intestines from duodenum to rectum were removed and injected with 4 ml of PBS pH 7.2, containing 0.1 mg/ml Soybean trypsin inhibitor, 50 mM EDTA and 1 mM PMSF. The intestinal contents were squeezed out into a petri dish on ice, homogenized using a spatula and transferred into a microfuge tube. The homogenate was vortexed and centrifuged at 13,000×g to separate the particulate material. The extracts were supplemented with 1 mM PMSF and 0.05% (w/v) NaN$_3$.

The protein bound radioactivity was determined by TCA precipitation. Two and half hours after intubation of iodinated dIgA and sIgA into the stomach, mice were sacrificed, and the intestinal washes were collected. Dimeric IgA and sIgA in intestinal washes were precipitated with 10% (w/v) TCA and with antibodies. To immunoprecipitate IgA, an aliquot of intestinal washes containing approximately 100,000 cpm of intestinal washes were incubated on ice with anti-α and anti-κ followed by protein G Sepharose (Sigma Chemical Co.) in PBS. After washing three times with PBS, the precipitates were counted. Electrophoresis sample buffer was added to the precipitates, boiled and half of the supernatant was analyzed by SDS-PAGE in 5% (w/v acrylamide) phosphate gels. To immunoprecipitate antigen specific IgA, approximately 100,000 cpm were incubated on ice with dansylated-BSA coupled to Sepharose beads (DNS-BSA-Sepharose). After washing, bound antibody was eluted by incubating the beads for 10 min. on ice in 30 µl of 3 mM ε-dansyl-L-lysine (Sigma Chemical Co.). Half of the eluted proteins was analyzed by SDS-PAGE in 5% (w/v acrylamide) phosphate gels. The gels were dried and exposed to Amersham Hyperfilm-MP for 48 hours.

7.2% of the intubated dIgA and 16.3% of the intubated sIgA were recovered in intestinal washes indicating that intact sIgA was more stable than dIgA, see Table 1.

TABLE 1

Recovery of Iodinated IgA.

| Protein | TCA precipitable cpm (10$^4$) | | Recovered cpm precipitated (10$^4$) | |
|---|---|---|---|---|
| | Intubated | Recovered (% of intubated) | DNS-BSA Sepharose | Anti-α + Anti-κ |
| dIgA | 343 | 24.6 (7.2) | 2.0 | 5.0 |
| sIgA | 320 | 52.0 (16.3) | 10.4 | 19.3 |

Consistent with more of the injected sIgA remaining intact in the intestine, a mixture of anti-α and anti-κ chain antiserum precipitated about 19.3×10$^4$ cpm of the sIgA but only 5.0×10$^4$ cpm of the dIgA (Table I). Similarly, antigen (DNS-BSA coupled to Sepharose) precipitated 10.4×10$^4$ cpm of the recovered sIgA but only 2.0×10$^4$ cpm of the recovered dIgA. SDS-PAGE analysis of the IgA precipitated with antigen showed a major band of Mr 55–60 kDa corresponding to Fab fragments in intestinal washes from mice given either sIgA or dIgA (FIG. 4B, Lane 6 and 7). The immunoprecipitates of anti-α and anti-κ chain showed a major band of Mr 55–60 kDa corresponding to Fab and Fc fragments with some minor higher molecular weight bands (FIG. 4B, Lane 3 and 4). The slower rate of elimination coupled with the recovery of more total and antigen specific sIgA than dIgA suggest that sIgA is more stable in the intestines than dIgA. However, both dIgA1 and sIgA1 appear to be susceptible to enzymes that cleave the IgA molecule in the hinge region.

In mice, serum dIgA is transported into bile by the pIgR expressed on the hepatocytes and this biliary IgA is emptied into the small intestine. To compare the stability of in vivo assembled sIgA with that of sIgA assembled by transfectant of the DNA fragment of the present invention, radiolabeled dIgA1 was injected i.v. into the tail vein of BALB/c mice. Three hours after injection, mice were sacrificed and the intestinal contents isolated. The antigen specific IgA precipitated from the intestinal washings showed a major band of Mr 55–60 kDa corresponding to Fab (FIG. 4B, Lane 3), similar to that found when dIgA or sIgA were introduced directly into the gastrointestinal tract. These results further confirm that the sIgA assembled in a single cell system is similar to sIgA assembled in vivo.

The development of a single mammalian cell system secreting sIgA makes it possible to produce the quantities of sIgA required for passive immunotherapy and represents a major advance over other methods for producing sIgA. This expression system also represents a major improvement over previous attempts to produce sIgA in *Nicotiana tabacum* plants (Ma et al., *Science* 268 716, 1995). The current use of human kappa, alpha, and SC genes also renders the resulting sIgA mostly human and, therefore, potentially more useful for in vivo therapy. Production of sIgA2, which lacks the protease sensitive hinge region of IgA1 may further enhance the in vivo stability of the sIgA molecule produced. Additionally, the large number of available IgA producing hybridomas with various pathogen specificities can be directly transfected with SC yielding hybridomas producing sIgA. With slight changes in the expression vectors or expression cell line, totally human sIgA can be produced in single cell tissue culture systems. Mammalian cells provide a means to produce sIgA in large quantities using established methods.

Secretory immunoglobulin A (sIga) in external secretions such as milk, saliva, tears and gastrointestinal and genitourinary tract secretions provides the first line of immune defense at the mucosal interface between the body proper and the outside environment. Therapeutic intervention at the mucosal surfaces is feasible by administering IgA to the nasopharangeal and gastro-intestinal mucosa to protect against pathogens. Monoclonal IgA antibodies directed against a single epitope on the surface of influenza virus or enteric bacteria have been shown to prevent respiratory disease and epithelial attachment and invasion of the intestines (Renegar et al., *J. Immunol.* 146 1972, 1991; Weltzin et al., *J. Cell Biology* 108 1673–1685, 1989; Winner et al., *Infect. Immun.* 59 977, 1991). Antibodies against Sendai virus, a respiratory pathogen in mice, applied directly to mucosal surfaces by nasal aspiration have been shown to provide protection (Mazanec et al., *J. Virol.* 61 2624, 1987). However, Mazanec et al. also showed that the monoclonal antibodies purified from hybridomas and used in these studies were degraded rapidly in the respiratory tract. It has been shown in vitro that sIgA is more resistant to bacterial proteases than serum derived monomeric IgA and polymeric IgA lacking SC suggesting that SC on IgA provides IgA resistance against proteases and thus renders sIgA more effective for therapeutic use.

In addition, immunotherapeutic treatments will require large quantities of sIgA. The development of one mammalian cell line synthesizing and secreting sIgA provides an optimal system to produce sIgA in large quantities.

The mechanisms of IgA protection are not well understood. However, there is considerable evidence to show that sIgA can crosslink microorganisms and prevent their adhesion to the mucosal epithelium. At present IgA monoclonal antibodies are being used in clinical trials for treatment of rotavirus and enterotoxigenic *Escherichia coli* infections. The hybridomas used in these trials can be transfected with the SC gene of the present invention. The sIgA produced by the resultant transfectants will be more effective and stable than the IgA monoclonals themselves.

The above description is of one embodiment of the present invention, however, it will be clear to those skilled in the art that various changes and modifications may be made without departing from the spirit of the invention. The invention is to be determined solely in terms of the following claims.

What is claimed is:

1. A method of producing secretory Ig (sIg) molecules comprising transfecting a non-plant cell producing an Ig with a polynucleotide encoding secretory component (SC) to form an SC transfected Ig producing cell, and culturing the SC transfected Ig producing cell so as to produce secretory Ig molecules.

2. The method of claim 1, further comprising collecting a supernatant produced by the cell.

3. The method of claim 2, further comprising purifying sIg from the supernatant.

4. The method of claim 1, wherein the secretory Ig and SC are derived from the same species of organism.

5. The method of claim 1, wherein the secretory Ig and SC are derived from different species of organism.

6. The method of claim 1, wherein the SC comprises the amino acid sequence shown in SEQ ID NO:4 or a congener thereof capable of associating with an Ig molecule.

7. The method of claim 1, wherein the non-plant cell endogenously produces Ig.

8. The method of claim 1, wherein the non-plant cell is genetically modified to produce Ig.

9. The method of claim 1, wherein the non-plant cell is a mammalian, avian, insect, bacterial or yeast cell.

10. The method of claim 9, wherein the mammalian cell is a human, rabbit, murine, rat or bovine cell.

11. The method of claim 1, wherein the non-plant cell is a myeloma cell, CHO cell, L cell, COS cell, fibroblast, MDCK cell, HT29 cell or a T84 cell.

12. The method of claim 1, wherein the Ig molecule is an IgA.

13. The method of claim 1, wherein the Ig molecule is a domain-modified IgA.

14. A method of producing secretory Ig (sIg) molecules comprising transfecting a non-plant cell with a polynucleotide encoding an Ig and with a polynucleotide encoding secretory component (SC) to form an SC transfected Ig producing cell, and culturing the SC transfected Ig producing cell so as to produce secretory Ig molecules.

15. The method of claim 14, wherein the Ig molecule is an IgA.

16. The method of claim 14, wherein the Ig molecule is a domain-modified IgA.

17. The method of claim 14, wherein the non-plant cell is a mannalian, avian, insect, bacterial or yeast cell.

18. The method of claim 17, wherein the mammalian cell is a human, rabbit, murine, rat or bovine cell.

19. The method of claim 14, wherein the non-plant cell is a myeloma cell, CHO cell, L cell, COS cell, fibroblast, MDCK cell, HT29 cell or a T84 cell.

* * * * *

UNITED STATES PATENT AND TRADEMARK OFFICE
CERTIFICATE OF CORRECTION

PATENT NO.   : 6,300,104 B1
DATED        : October 9, 2001
INVENTOR(S)  : Sherie L. Morrison and Kote R. Chintalacharuvu It is certified that error appears in the above-identified patent and that said Letters Patent is hereby corrected as shown below:

Title page,
Item [57], ABSTRACT,
Line 5, "fonn" should read -- form --.

Signed and Sealed this

Twenty-eighth Day of January, 2003

JAMES E. ROGAN
*Director of the United States Patent and Trademark Office*

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 30 base pairs
      (B) TYPE: nucleic acid
      (C) STRANDEDNESS: double
      (D) TOPOLOGY: linear (ii) MOLECULE TYPE: cDNA to mRNA (xi) SEQUENCE DESCRIPTION: SEQ ID NO:1:

GGGCAGAACG GTGACCATCA ACTGCCCTTT        30

(2) INFORMATION FOR SEQ ID NO:2:

(i) SEQUENCE CHARACTERISTICS:
      (A) LENGTH: 42 base pairs
      (B) TYPE: nucleic acid
      (C) STRANDEDNESS: double
      (D) TOPOLOGY: linear (ii) MOLECULE TYPE: cDNA to mRNA (xi) SEQUENCE DESCRIPTION: SEQ ID NO:2:

AAGGAATTCC TACTCTGCAA AAAGCCTGGG GTCCTGAATG GC        42

(2) INFORMATION FOR SEQ ID NO:3:

(i) SEQUENCE CHARACTERISTICS:
      (A) LENGTH: 1839 base pairs
      (B) TYPE: nucleic acid
      (C) STRANDEDNESS: double
      (D) TOPOLOGY: linear (ii) MOLECULE TYPE: cDNA to mRNA (xi) SEQUENCE DESCRIPTION: SEQ ID NO:3:

ATGCTGCTCT TCGTGCTCAC CTGCCTGCTG GCGGTCTTCC CAGCCATCTC CACGAAGAGT        60

| | |
|---|---|
| CCCATATTTG GTCCCGAGGA GGTGAATAGT GTGGAAGGTA ACTCAGTGTC CATCACGTGC | 120 |
| TACTACCCAC CCACCTCTGT CAACCGGCAC ACCCGGAAGT ACTGGTGCCG GCAGGGAGCT | 180 |
| AGAGGTGGCT GCATAACCCT CATCTCCTCG GAGGGCTACG TCTCCAGCAA ATATGCAGGC | 240 |
| AGGGCTAACC TCACCAACTT CCCGGAGAAC GGCACATTTG TGGTGAACAT TGCCCAGCTG | 300 |
| AGCCAGGATG ACTCCGGGCG CTACAAGTGT GGCCTGGGCA TCAATAGCCG AGGCCTGTCC | 360 |
| TTTGATGTCA GCCTGGAGGT CAGCCAGGGT CCTGGGCTCC TAAATGACAC TAAAGTCTAC | 420 |
| ACAGTGGACC TGGGCAGAAC GGTGACCATC AACTGCCCTT TCAAGACTGA GAATGCTCAA | 480 |
| AAGAGGAAGT CCTTGTACAA GCAGATAGGC CTGTACCCTG TGCTGGTCAT CGACTCCAGT | 540 |
| GGTTATGTGA ATCCCAACTA TACAGGAAGA ATACGCCTTG ATATTCAGGG TACTGGCCAG | 600 |
| TTACTGTTCA GCGTTGTCAT CAACCAACTC AGGCTCAGCG ATGCTGGGCA GTATCTCTGC | 660 |
| CAGGCTGGGG ATGATTCCAA TAGTAATAAG AAGAATGCTG ACCTCCAAGT GCTAAAGCCC | 720 |
| GAGCCCGAGC TGGTTTATGA AGACCTGAGG GGCTCAGTGA CCTTCCACTG TGCCCTGGGC | 780 |
| CCTGAGGTGG CAAACGTGGC CAAATTTCTG TGCCGACAGA GCAGTGGGGA AAACTGTGAC | 840 |
| GTGGTCGTCA ACACCCTGGG GAAGAGGGCC CCAGCCTTTG AGGGCAGGAT CCTGCTCAAC | 900 |
| CCCCAGGACA AGGATGGCTC ATTCAGTGTG GTGATCACAG GCCTGAGGAA GGAGGATGCA | 960 |
| GGGCGCTACC TGTGTGGAGC CCATTCGGAT GGTCAGCTGC AGGAAGGCTC GCCTATCCAG | 1020 |
| GCCTGGCAAC TCTTCGTCAA TGAGGAGTCC ACGATTCCCC GCAGCCCCAC TGTGGTGAAG | 1080 |
| GGGGTGGCAG GAAGCTCTGT GGCCGTGCTC TGCCCCTACA ACCGTAAGGA AAGCAAAAGC | 1140 |
| ATCAAGTACT GGTGTCTCTG GAAGGGGCC CAGAATGGCC GCTGCCCCT GCTGGTGGAC | 1200 |
| AGCGAGGGGT GGGTTAAGGC CCAGTACGAG GGCCGCCTCT CCCTGCTGGA GGAGCCAGGC | 1260 |
| AACGGCACCT TCACTGTCAT CCTCAACCAG CTCACCAGCC GGGACGCCGG CTTCTACTGG | 1320 |
| TGTCTGACCA ACGGCGATAC TCTCTGGAGG ACCACCGTGG AGATCAAGAT TATCGAAGGA | 1380 |
| GAACCAAACC TCAAGGTACC AGGGAATGTC ACGGCTGTGC TGGGAGAGAC TCTCAAGGTC | 1440 |
| CCCTGTCACT TTCCATGCAA ATTCTCCTCG TACGAGAAAT ACTGGTGCAA GTGGAATAAC | 1500 |
| ACGGGCTGCC AGGCCCTGCC CAGCCAAGAC GAAGGCCCCA GCAAGGCCTT CGTGAACTGT | 1560 |
| GACGAGAACA GCCGGCTTGT CTCCCTGACC CTGAACCTGG TGACCAGGGC TGATGAGGGC | 1620 |
| TGGTACTGGT GTGGAGTGAA GCAGGGCCAC TTCTATGGAG AGACTGCAGC CGTCTATGTG | 1680 |
| GCAGTTGAAG AGAGGAAGGC AGCGGGGTCC CGCGATGTCA GCCTAGCGAA GGCAGACGCT | 1740 |
| GCTCCTGATG AGAAGGTGCT AGACTCTGGT TTTCGGGAGA TTGAGAACAA AGCCATTCAG | 1800 |
| GATCCCAGGC TTTTTGCAGA GTAGGAATTC CTGCAGCCC | 1839 |

(2) INFORMATION FOR SEQ ID NO:4:

(i) SEQUENCE CHARACTERISTICS:
        (A) LENGTH: 608 amino acids
        (B) TYPE: amino acid
        (C) STRANDEDNESS: unknown
        (D) TOPOLOGY: linear (ii) MOLECULE TYPE: protein (xi) SEQUENCE DESCRIPTION: SEQ ID NO:4:

```
Met Leu Leu Phe Val Leu Thr Cys Leu Leu Ala Val Phe Pro Ala Ile
 1               5                  10                  15
Ser Thr Lys Ser Pro Ile Phe Gly Pro Glu Glu Val Asn Ser Val Glu
                20                  25                  30
```

-continued

```
Gly Asn Ser Val Ser Ile Thr Cys Tyr Tyr Pro Pro Thr Ser Val Asn
         35                  40                  45

Arg His Thr Arg Lys Tyr Trp Cys Arg Gln Gly Ala Arg Gly Gly Cys
     50                  55                  60

Ile Thr Leu Ile Ser Ser Glu Gly Tyr Val Ser Ser Lys Tyr Ala Gly
65                  70                  75                  80

Arg Ala Asn Leu Thr Asn Phe Pro Glu Asn Gly Thr Phe Val Val Asn
                 85                  90                  95

Ile Ala Gln Leu Ser Gln Asp Ser Gly Arg Tyr Lys Cys Gly Leu
                100                 105                 110

Gly Ile Asn Ser Arg Gly Leu Ser Phe Asp Val Ser Leu Glu Val Ser
         115                 120                 125

Gln Gly Pro Gly Leu Leu Asn Asp Thr Lys Val Tyr Thr Val Asp Leu
    130                 135                 140

Gly Arg Thr Val Thr Ile Asn Cys Pro Phe Lys Thr Glu Asn Ala Gln
145                 150                 155                 160

Lys Arg Lys Ser Leu Tyr Lys Gln Ile Gly Leu Tyr Pro Val Leu Val
                165                 170                 175

Ile Asp Ser Ser Gly Tyr Val Asn Pro Asn Tyr Thr Gly Arg Ile Arg
            180                 185                 190

Leu Asp Ile Gln Gly Thr Gly Gln Leu Leu Phe Ser Val Val Ile Asn
        195                 200                 205

Gln Leu Arg Leu Ser Asp Ala Gly Gln Tyr Leu Cys Gln Ala Gly Asp
    210                 215                 220

Asp Ser Asn Ser Asn Lys Lys Asn Ala Asp Leu Gln Val Leu Lys Pro
225                 230                 235                 240

Glu Pro Glu Leu Val Tyr Glu Asp Leu Arg Gly Ser Val Thr Phe His
                245                 250                 255

Cys Ala Leu Gly Pro Glu Val Ala Asn Val Ala Lys Phe Leu Cys Arg
            260                 265                 270

Gln Ser Ser Gly Glu Asn Cys Asp Val Val Asn Thr Leu Gly Lys
        275                 280                 285

Arg Ala Pro Ala Phe Glu Gly Arg Ile Leu Leu Asn Pro Gln Asp Lys
    290                 295                 300

Asp Gly Ser Phe Ser Val Val Ile Thr Gly Leu Arg Lys Glu Asp Ala
305                 310                 315                 320

Gly Arg Tyr Leu Cys Gly Ala His Ser Asp Gly Gln Leu Gln Glu Gly
                325                 330                 335

Ser Pro Ile Gln Ala Trp Gln Leu Phe Val Asn Glu Glu Ser Thr Ile
            340                 345                 350

Pro Arg Ser Pro Thr Val Val Lys Gly Val Ala Gly Ser Ser Val Ala
        355                 360                 365

Val Leu Cys Pro Tyr Asn Arg Lys Glu Ser Lys Ser Ile Lys Tyr Trp
    370                 375                 380

Cys Leu Trp Glu Gly Ala Gln Asn Gly Arg Cys Pro Leu Leu Val Asp
385                 390                 395                 400

Ser Glu Gly Trp Val Lys Ala Gln Tyr Glu Gly Arg Leu Ser Leu Leu
                405                 410                 415

Glu Glu Pro Gly Asn Gly Thr Phe Thr Val Ile Leu Asn Gln Leu Thr
            420                 425                 430

Ser Arg Asp Ala Gly Phe Tyr Trp Cys Leu Thr Asn Gly Asp Thr Leu
        435                 440                 445

Trp Arg Thr Thr Val Glu Ile Lys Ile Ile Glu Gly Glu Pro Asn Leu
```

-continued

```
              450                 455                 460
Lys Val Pro Gly Asn Val Thr Ala Val Leu Gly Glu Thr Leu Lys Val
465                 470                 475                 480

Pro Cys His Phe Pro Cys Lys Phe Ser Ser Tyr Glu Lys Tyr Trp Cys
                485                 490                 495

Lys Trp Asn Asn Thr Gly Cys Gln Ala Leu Pro Ser Gln Asp Glu Gly
                500                 505                 510

Pro Ser Lys Ala Phe Val Asn Cys Asp Glu Asn Ser Arg Leu Val Ser
            515                 520                 525

Leu Thr Leu Asn Leu Val Thr Arg Ala Asp Glu Gly Trp Tyr Trp Cys
        530                 535                 540

Gly Val Lys Gln Gly His Phe Tyr Gly Glu Thr Ala Ala Val Tyr Val
545                 550                 555                 560

Ala Val Glu Glu Arg Lys Ala Ala Gly Ser Arg Asp Val Ser Leu Ala
                565                 570                 575

Lys Ala Asp Ala Ala Pro Asp Glu Lys Val Leu Asp Ser Gly Phe Arg
                580                 585                 590

Glu Ile Glu Asn Lys Ala Ile Gln Asp Pro Arg Leu Phe Ala Glu Glx
            595                 600                 605
```